US008903478B2

(12) United States Patent
MacAdam et al.

(10) Patent No.: US 8,903,478 B2
(45) Date of Patent: Dec. 2, 2014

(54) HIGH DENSITY ATRIAL FIBRILLATION CYCLE LENGTH (AFCL) DETECTION AND MAPPING SYSTEM

(71) Applicant: C.R. Bard Inc., Murray Hill, NJ (US)

(72) Inventors: David P. MacAdam, Millbury, MA (US); Minoru Mashimo, Windham, NH (US); Sylvain Fanier, La Celle (FR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/666,652

(22) Filed: Nov. 1, 2012

(65) Prior Publication Data

US 2013/0303879 A1     Nov. 14, 2013

Related U.S. Application Data

(63) Continuation of application No. 12/418,601, filed on Apr. 5, 2009, now abandoned, which is a continuation of application No. 11/120,633, filed on May 2, 2005, now abandoned.

(60) Provisional application No. 60/572,281, filed on May 17, 2004.

(51) Int. Cl.
    *A61B 5/046*     (2006.01)
    *A61B 18/14*     (2006.01)
    *A61B 5/00*     (2006.01)
    *A61B 18/00*     (2006.01)

(52) U.S. Cl.
CPC ............. *A61B 5/046* (2013.01); *A61B 18/1492* (2013.01); *A61B 5/7257* (2013.01); *A61B 2018/00839* (2013.01)
USPC ......................................................... 600/515

(58) Field of Classification Search
None
See application file for complete search history.

(56) References Cited

U.S. PATENT DOCUMENTS

| | | | |
|---|---|---|---|
| 4,945,477 A * | 7/1990 | Edwards | 600/518 |
| 5,425,373 A | 6/1995 | Causey, III | |
| 5,433,198 A | 7/1995 | Desai | |
| 5,595,183 A | 1/1997 | Swanson et al. | |
| 5,687,737 A | 11/1997 | Branham et al. | |
| 5,771,898 A | 6/1998 | Marinello | |
| 5,772,603 A | 6/1998 | Ohlsson et al. | |
| 5,855,592 A * | 1/1999 | McGee et al. | 607/4 |
| 6,081,746 A * | 6/2000 | Pendekanti et al. | 607/5 |

(Continued)

OTHER PUBLICATIONS

Gaspo, Rania, Ralph F. Bosch, Mario Talajic, and Stanley Nattel. "Functional Mechanisms Underlying Tachycardia-Induced Sustained Atrial Fibrillation in a Chronic Dog Model—Gaspo Et Al. 96 (11): 4027." Circulation. American Heart Association, Inc., 1997. Web. Jun. 1, 2011. <http://circ.ahajournals.org/cgi/content/short/96/11/4027>.

(Continued)

*Primary Examiner* — Brian T Gedeon
(74) *Attorney, Agent, or Firm* — Seager, Tufte & Wickhem, LLC

(57) ABSTRACT

Systems and methods to assist in locating the focus of an atrial fibrillation include the association of atrial fibrillation cycle length values and statistics relating thereto with temporal locations on an electrogram of a given electrode, and/or the coordination of electrode locations with respective the spectral analyses of electrogram signals and further parameters and statistics relating thereto. Ablation therapy can proceed under guidance of such information.

30 Claims, 10 Drawing Sheets

(56) References Cited

U.S. PATENT DOCUMENTS

| | | | |
|---|---|---|---|
| 6,085,116 | A | 7/2000 | Pendekanti et al. |
| 6,188,407 | B1 | 2/2001 | Smith et al. |
| 6,223,073 | B1 | 4/2001 | Seegobin |
| 6,292,691 | B1 | 9/2001 | Pendekanti et al. |
| 6,292,695 | B1 | 9/2001 | Webster, Jr. et al. |
| 6,937,887 | B2 * | 8/2005 | Bock .............................. 600/519 |
| 6,990,370 | B1 | 1/2006 | Beatty et al. |
| 7,263,397 | B2 | 8/2007 | Hauck et al. |
| 2003/0023130 | A1 | 1/2003 | Ciaccio et al. |
| 2007/0073179 | A1 | 3/2007 | Afonso et al. |
| 2007/0232949 | A1 | 10/2007 | Saksena |

OTHER PUBLICATIONS

Shimizu, Akihiko & Yamagata, Toshihiko & Esato, Masahiro & Doi, Masahiro & Kakugawa, Hiroyuki & Kametani, Ryousuke & Inoue, Noriko & Kanemoto, Masashi & Matsuzaki, Masunori. *New method of determining the atrial fibrillation cycle length during human atrial fibrillation*. Journal of cardiovascular electrophysiology. 2003. pp. 965-970.

Flynn, Simon P., Derick M. Todd, Julian C. Hobbs, Karen L. Armstrong, Adam P. Fitzpatrick, and Clifford J. Garratt. *Effect of Amiodarone on Dispersion of Atrial Refractoriness and Cycle Length in Patients with Atrial Fibrillation*. Journal of cardiovascular electrophysiology. vol. 14, No. 5. 2003. pp. 485-491.

* cited by examiner

HIGH DENSITY ATRIAL FIBRILLATION CYCLE LENGTH (AFCL) DETECTION AND MAPPING SYSTEM

CROSS-REFERENCE TO RELATED APPLICATION

The present application is a continuation of U.S. patent application Ser. No. 12/418,601, filed Apr. 5, 2009, which is a continuation of U.S. patent application Ser. No. 11/120,633, filed May 2, 2005, which claims the benefit of U.S. Patent Application Ser. No. 60/572,281, filed May 17, 2004, each of which is hereby incorporated by reference in its entirety.

FIELD OF THE INVENTION

The present invention relates to intervention and treatment of heart conditions such as atrial arrhythmias and more particularly atrial fibrillation with regard to characteristics of the heart tissue itself, and more particularly the present invention concerns the use of atrial fibrillation cycle length determinations in the mapping, diagnosis, treatment and prevention and intervention of atrial fibrillation as well as computer-implemented systems and interfaces relating thereto.

BACKGROUND OF THE INVENTION

Atrial fibrillation together with atrial flutter is the most commonly sustained arrhythmia found in clinical practice. Although there has been an increased awareness in the last several years of the potentially serious clinical consequences of both arrhythmias, their basic electrophysiological mechanisms and optimal management strategies only recently have been understood. Atrial fibrillation (AF) involves rapid and chaotic beating of the individual fibers of the heart muscle such that synchronous contraction is not maintained. This inevitably results in that part of the heart ceasing to pump blood, which in turn can lead to embolic stroke. Atrial fibrillation is characterized by the presence of multiple reentrant circuits that may be active simultaneously, precluding the synchronous activation of enough atrial myocardium to generate an identifiable p wave or coordinated atrial contraction. Either a sinus impulse or a stable atrial flutter reentrant circuit (flutter wave) may degenerate into the multiple reentrant circuits (multiple wavelets) characteristic of atrial fibrillation, (Cox et al., J. Thoracic. Cardiovas. Surg. 101: 402-405 1991).

Atrial fibrillation currently afflicts over three million persons in the United States. (Cox et al., J. Thoracic. Cardiovas. Surg. 101: 402-405 1991). It is the most commonly sustained arrhythmia, increasing progressively in prevalence with advancing age, and occurring in 2%-4% of the population over the age of 60. Atrial fibrillation is associated with atherosclerosis, chronic rheumatic heart disease, hypertensive heart disease and stroke.

Our current understanding is that atrial fibrillation (AF) is initiated most often by a focal trigger from the orifice of or from within one of the pulmonary veins. Though mapping and ablation of these triggers appears to be curative in most patients with paroxysmal AF, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger. By electrically isolating one or more of the triggers in the pulmonary veins from the left atrium with a lesion, firing from within those veins would be unable to reach the body of the atrium, and thus could not trigger atrial fibrillation.

There are several catheter-based therapeutic modalities currently being used for the treatment of atrial fibrillation. However, there is still recurrence of atrial fibrillation after catheter ablation. It is difficult to predict the long-term success or recurrence. In the attempt to increase the long-term success rate, several modified therapies are proposed and practiced, for example, adding one or more linear lesions in the left atrium, the right atrium, or both, and creating a larger area of lesions that surround the left atrial tissue and junction of the pulmonary veins. However, the mechanism of this kind of approach is not clear and may in fact be destructive to mechanical function of the heart in the long term. Therefore, what is needed in the art is a more predictive approach and tools therefor that are able to evaluate the substrate of atrial arrhythmias, which include atrial fibrillation, and to provide direction for future intervention in addition to the elimination of the arrhythmic foci. Furthermore, what is needed in the art is a predictive parameter that can indicate long-term success likelihood to the electrophysiologist.

U.S. Pat. No. 6,081,746 discusses AFCL in the context of pacing the heart. This patent recognizes that the AFCL varies with regions of the heart, but suggests that the AFCL value sensed at the Bachmann's Bundle is adequate for use in pacing despite variations that may exist through the heart tissue.

Atrial cycle length is an important intrinsic property of atrial tissue. It provides a characterization of the substrate of the atrial tissue of AF patients. However, due to the chaotic nature of waveforms during AF, it is difficult to interpret cycle length of atrial tissue on a beat-by-beat basis. Rather, an average atrial fibrillation cycle length ("AFCL") has been manually calculated by electrophysiologists to determine the vulnerability of atrial tissue to AF trigger. It also is used to aid operators in deciding whether or not to create any or any additional lesions using an ablation catheter or other instrument. To determine the Atrial Fibrillation Cycle Length (AFCL), EP physicians have used a conventional catheter by moving the catheter within and around the atrium to survey the targeted atrial tissue; the AFCL is manually calculated by taking the total cycle length at a certain period, e.g. 2 seconds, divided by the total peaks of atrial activation. Electrocardiograms are analyzed carefully to reject low-amplitude potentials and to detect double potentials associated with block, correlation with the surface ECG was used to eliminate the ventricular electrocardiogram. The procedure is subjective, tedious and is time-consuming and has not provided a convenient, rapid, and repeatable approach to evaluating and utilizing AFCL determinations. The present invention addresses one or more of these and other deficiencies in the prior art.

SUMMARY OF INVENTION

The invention concerns the automated determination of atrial fibrillation cycle length values and the manipulation and derivation of further parameters and statistics therefrom. Electrocardiogram signals can be annotated using this information and one or more maps can be created which coordinate location information of indwelling catheter electrodes with AFCL data and its derivatives. Ablation therapy can proceed under guidance of such maps.

The invention also concerns spectral analysis of electrogram signals to assist in the identification of atrial fibrillation, and encompasses the simultaneous display across locations in one or more cardiac chambers of information concerning the dominant frequency and/or AFCL, and/or other parameters and statistics. Consistent with this aspect of the invention, an ablation and mapping procedure comprises percutaneously advancing a catheter into at least one of the atria, the catheter having multiple electrodes supported along its distal portion. One or more locations of the electrodes within the atria are associated in a memory of a machine. Electrocardiogram signals associated with at least one electrode of the catheter at one or more of the locations are captured for at least a prescribed time period. The electrogram signals are transformed into a frequency domain representation for at least a portion of the captured electrocardiogram signals over at least the prescribed time period. The frequency domain representation is coordinated with respective locations of the multiple electrodes to define a set of data points which are output on a display.

Also consistent with this aspect of the invention, a system for performing diagnostics on electrocardiogram data comprises a monitor operative to display electrophysiology data, an input configured to accept a time-domain representation of one or more electrocardiogram (EGM) signals obtained by electrodes at respective different locations within the heart, a processor connected to receive the signals from the input over a time interval, and software executable by the processor. The software is configured to transform the time-domain EGM signals into a frequency domain representation over at least a portion of the time interval and to cause information related to the frequency domain representation to be displayed on the monitor in association with said respective different locations.

In accordance with another aspect of the invention, a method for annotating an electrocardiogram with an atrial fibrillation cycle length (AFCL) value that is displayable on a display of an electrophysiology system is provided. That method comprises providing an electrocardiogram signal within the electrophysiology system, accepting input to the electrophysiology system to define a time segment of interest within the electrocardiogram signal, locating successive activation signals within the time segment of interest on each electrocardiogram signal, determining one or more AFCL values using the located successive activation signals, and associating on the display of the electrophysiology system at least one of the determined AFCL values together with the electrocardiogram signal.

In accordance with yet another aspect of the invention, an electrophysiology system comprises inputs configured to receive plural electrocardiogram signals from multiple intracardiac electrodes that have been disposed at respective locations within a heart, software operative to apply a finite impulse response (FIR) filter to the plural electrocardiogram signals so as to output a location along a time-axis of one or more activation signals detected in the plural electrocardiogram signals and to determine one or more atrial fibrillation cycle length (AFCL) values, and an output configured to display the plural electrocardiogram signals associated with each respective intracardiac electrode on a display. The output comprises a first window configured to display along the time-axis the plural electrocardiogram signals in association with at least one of the one or more AFCL values, and a second window configured to display a map that coordinates at least one determined AFCL value with the locations within the heart of the respective intracardiac electrodes.

In accordance with still another aspect of the invention, an ablation and mapping procedure is provided which comprises percutaneously advancing a catheter into at least one of the atria, the catheter having multiple electrodes supported along a distal portion thereof, associating in a memory of a machine one or more locations of the electrodes within the at least one of the atria, and capturing electrocardiogram signals associated with at least one electrode of the catheter at one or more of the locations. For at least a portion of the captured electrocardiogram signals, this method calculates one or more discrete atrial fibrillation cycle length (AFCL) values. The calculated discrete AFCL values are coordinated with respective locations of the multiple electrodes to define a set of data points, a continuous isochronal representation of AFCL is extrapolated from the set of data points, and the extrapolated representation is output on a display.

In accordance with a further aspect of the invention, an electrophysiology system comprises a monitor operative to display electrophysiology data, an input configured to accept signals from plural cardiac leads, a processor configured to receive the signals from the input and to influence the electrophysiology data displayable on the monitor, and software executable by the processor. The software in accordance with this aspect of the invention is configured to operate upon signals from the plural cardiac leads so as to determine at least one value representative of an atrial fibrillation cycle length (AFCL) and to cause information related to the at least one value to be displayed on the monitor.

These and other aspects, features and advantages will be apparent from the accompanying detailed description and Drawing Figures of certain embodiments of the invention.

BRIEF DESCRIPTION OF THE DRAWING FIGURES

These and various other features and aspects of the present invention will be readily understood with reference to the following detailed description taken in conjunction with the accompanying drawings, in which like or similar numbers are used throughout, and in which:

FIG. 3A is a schematic illustration of a data structure that can be used in implementing the preferred embodiment.

DETAILED DESCRIPTION OF CERTAIN EMBODIMENTS

By way of overview and introduction, when heart cells are activated, the electrical polarization caused by the normal voltage difference of about 90 mV between the inside and outside of the cells collapses and the heart tissue is said to "depolarize." Depolarized heart tissue which has not been given adequate time to re-establish its normal voltage difference and will not produce a new activation in response to a further intrinsic or extrinsic electrical stimulus is referred to as refractory tissue. After depolarization, heart cells begin to re-establish the normal voltage difference ("repolarization"). Tissue which has been afforded an adequate length of time to re-establish a sufficiently large voltage difference to once again become susceptible to depolarization is no longer refractory. The time interval which is required after a cell has been depolarized until it is again non-refractory is called the refractory period. In a fibrillating heart, depolarization wavefronts move through the myocardium along re-entrant pathways in a chaotic manner. The time period required for a given depolarization wavefront to traverse and complete a circuit along some re-entrant pathway of tissue in the atrium is the atrial fibrillation cycle length (AFCL). Due to variations in the substrate of cardiac tissue, certain locations can have AFCLs that differ enough so as to disturb the main course of the activation wave. The period following an activation when tissue becomes non-refractory again is referred to as the "excitable gap." The excitable gap follows the refractory period of the AFCL.

Figure 1:
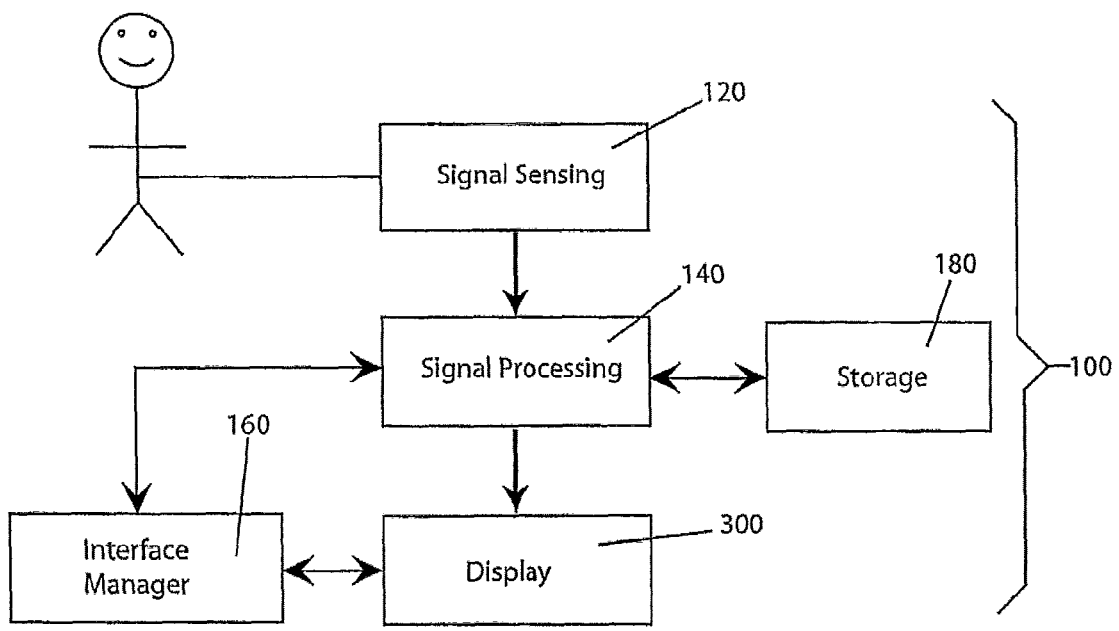
FIG. 1 is a schematic diagram of a system configured to implement the methods of the present invention.

Referring now to the drawings, and particularly to FIG. 1, there is shown an EP system 100 for receiving and processing electrical signals according to one illustrative embodiment of the present invention. In the illustrated embodiment, the EP system 100 includes a signal sensing unit 120, which may take different forms, such as a standard 12-lead ECG, intracardiac lead, or combination thereof. Sensors useful for collecting electrophysiological data on a fibrillating atrium or ventricle that are useful for determining local fibrillation cycle lengths according to the principles of this invention include those that are conventional in the art. Such sensors generally comprise a conventional sensing electrode or electrodes, positioned in or on the heart in locations suitable for monitoring the electrical activity associated with a fibrillating heart and producing analog electrocardiogram ("EGM" or "electrogram") signals in response thereto. The electrodes can be mounted on a multiple-electrode expandable mesh-like catheter, fixed size and adjustable circular loop catheter, basket catheter, balloon-like catheter, longitudinal shaft catheter, etc. Multiple-channel electrograms can be collected at different anatomic locations including multi-chamber locations in the heart via the multiple-electrode catheter. An amplifier operatively connected so as to amplify the EGM signals and a waveform digitizer that digitizes the EGM signals to produce digital EGM data provide a digital data stream upon which signal processing can be performed.

The signal sensing unit 120 is electrically connected to a signal processing device 140, which receives the sensed signals from the unit 120 and is configured or programmed to process the digital EGM data in accordance with the selected mode of operation, be it diagnostic, therapeutic, mapping, or intervention. The signal processing device ("signal processor" or "processor") 140 is preferably connected to a suitable display 300, which will present the processed signals to a clinician or other interested person, under control of an interface manager 160 which may be combined with the signal processing device 140 as a single hardware unit. Information can be stored and recalled from a storage device 180. Preferably the signal processing device 140, interface manager 160, and display 300 comprise the EP LabSystem (trademark) Pro of C.R. Bard, Inc., Murray Hill, N.J., or the like. The EP LabSystem (trademark) Pro supports a variety of data gathering and processing functions that are standard in electrophysiology procedures, and can be configured to implement the processes described herein through software (e.g., modules, procedures, functions, or objects) or firmware. The processor 140 communicates with the memory or storage 180 which configures the processor to implement the processes of the present invention under control of the interface manger 160.

In one illustrative embodiment, the special features of the system of the present invention are implemented, in part, by a processor using program information stored in a memory of the signal processing device 140 that is configured to process electrophysiologic information related to the arrhythmic cardiac substrate. The processor 140 can access one or more files or software, as necessary, to implement the required functions, as described in the accompanying flow diagrams. The interface manager 160 enables the operator to interact with graphical objects rendered on the display 300 using a conventional pointer device or touch screen so as to change the values of their properties, invoke their methods, instantiate new objects, or terminate active processes.

Figure 2:
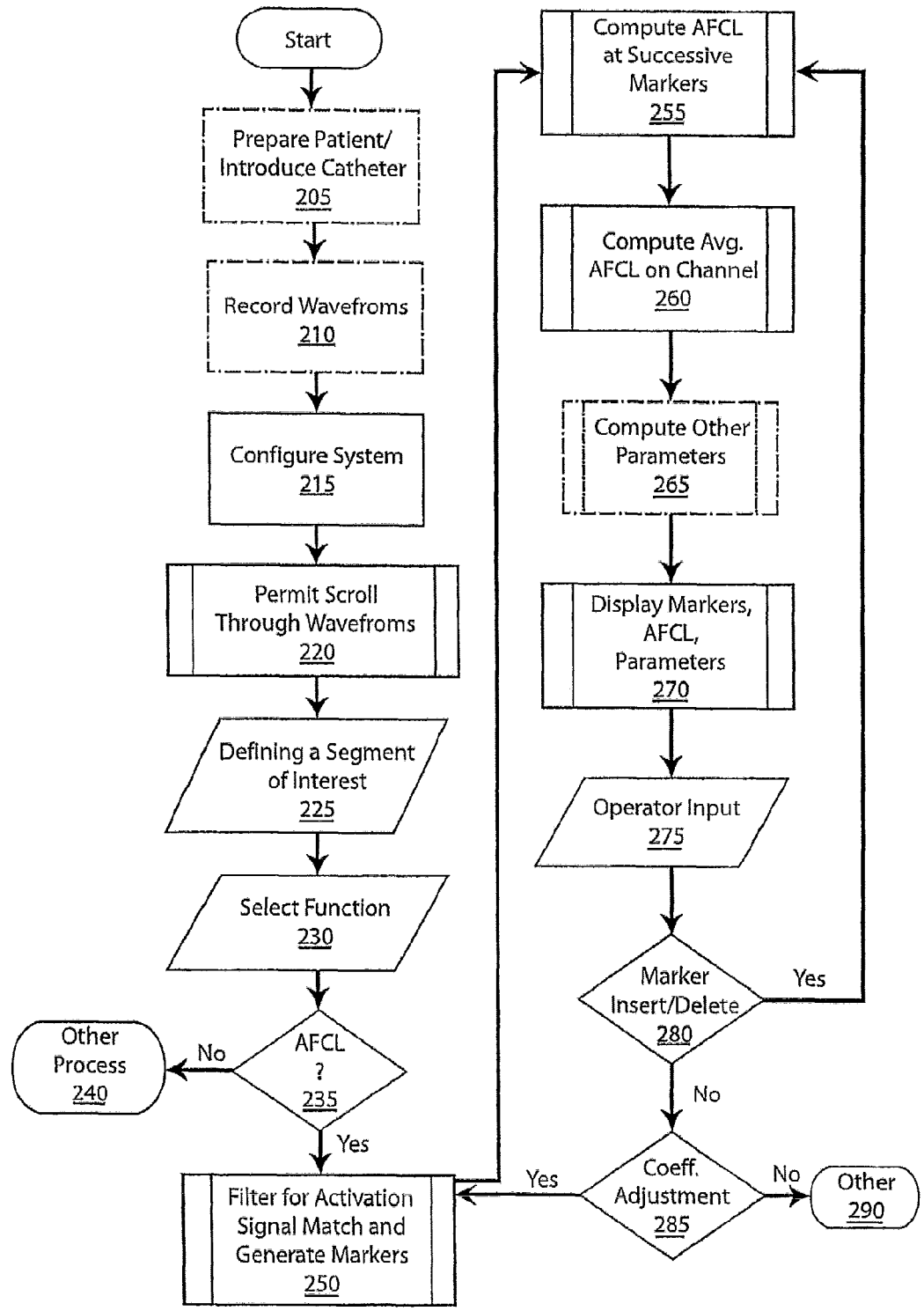
FIG. 2 is a flow diagram of a method in accordance with an aspect of the invention that determines and presents AFCL data.

Referring now to FIG. 2, the operation of the signal processing device 140 in determining AFCL values is described in conjunction with the above structural description of the EP system 100.

At step 205, a patient can be prepared for an electrophysiological study or treatment, in accordance with convention, including having one or more catheters introduced into his or her heart, at least one of the catheters including sensing electrodes such as noted above. The sensing electrodes can be introduced and positioned at predefined locations within a heart or can be tracked and positioned using flouroscopy, MRI, CT, ultrasound imaging or echoing, impedance, or electromagnetic localization techniques (e.g., voltage, current, or magnetic field gradients), as known in the art, and can be in tissue-contacting or floating relation to the heart wall, if internally positioned. EGMs that are captured by the sensing electrodes can be recorded or buffered at step 210 into the memory of the EP system 100. These steps can precede the AFCL determinations or can be part of a live, that is, "real-time," procedure.

At step 215 the EP system operator provides configuration parameters to the EP system 100 for the AFCL determination. The configuration step can be initiated automatically upon selection by the operator of the AFCL-determination function. The configuration parameters can include, among other settings, an identification of (1) which of the electrograms are to be analyzed, (2) the time epoch to be tracked (e.g., a one, five or thirty second interval), (3) a filter used to digitally process the electrogram signals and identify each new cycle in the interval, and (4) any filter settings that may be specific to (that is, trained for) the patient. Configuration also can be set in accordance with default values to permit the operator to make customizations while the AFCL routines are actively processing the sensed EGM data.

Insofar as there may be multiple sensing electrodes each displayable on a different channel of the EP system 100, during the configuration step, the operator can identify certain channels on which the AFCL analysis is to be made. The channels include data from sensing electrodes at particular locations within the heart—which locations do not change over the sampling interval, and so the selection of channels may be assisted with location information that correlates the location of a given sensor with its present location within the heart.

If the time epoch is defined in the configuration step, then an operator need only identify the beginning or end of an electrogram segment that is of interest, as described below, in order to define a segment of interest ("SOI") over which the AFCL determinations are made.

The filter of the preferred embodiment is a finite impulse response ("FIR") filter. The FIR filter can be configured to detect activation signals (e.g., depolarization wavefronts passing through a particular cardiac site) within the electrogram through the use of digital signal processing. Detection of an activation signal with a FIR filter comprises a non-zero output signal (known as "ringing") that constitutes the impulse response of the filter to an impulse received at its inputs. The "impulse response" of the FIR filter is defined by its set of FIR coefficients, and in the preferred embodiment, the FIR has 5 taps, that is, five coefficient/delay pairs which are accumulated into an output signal. Thus, during the configuration step, the impulse response of the filter is defined by setting the filter's coefficient values. The impulse response of a FIR is considered "finite" because there is no feedback in the filter. Consequently, an impulse input to the filter (that is, a sample of value "1" followed by many samples of value "0"), will eventually result in an output that is all zeros. However, the initial impulse will cause a non-zero "ringing" output which fades to zero after the sample has made its way in the delay line past all the coefficients. An appropriate setting of the coefficient values of the FIR is necessary in order to detect activation signals. A linear filter and appropriately selected coefficients are preferred and can even preserve phase information which may be mapped in accordance with a further aspect of the invention.

A default set of values can be set for the coefficients that defines an impulse response that is consistent with empirically monitored activation signals. In other words, the filter can be trained against a set of known data, with the coefficients adjusted so that the filter rings in response to a prescribed electrical signal pattern corresponding to a known activation signal. Thus, for example, electrogram data from a number of persons of the same age and health can be used to train the response of a FIR filter which results in a set of coefficient values that can be stored in the EP system 100 and recalled during the configuration step as a default setting. In this way, patient-independent data can be used to configure the FIR filter to detect activation signals. The operator can make adjustments from the default values such as the number or magnitude of the rings before detecting the event as an activation, or the number of points of deflection from a nominal baseline value in the EGM signal. Alternatively or in addition, patient-specific data can be used to train the FIR filter or fine-tune its response to a given patient. Yet another alternative is to use artificial intelligence to compare electrograms against a knowledge database of previously-classified signals, and create a filter (that is, a set of coefficient values) that is dynamically tuned with regard to the electrogram signals being observed.

As discussed below, the filter's coefficient values can be readily changed by the operator if the operator has a particular perspective concerning which events constitute an activation or when an activation commences.

Figure 3:
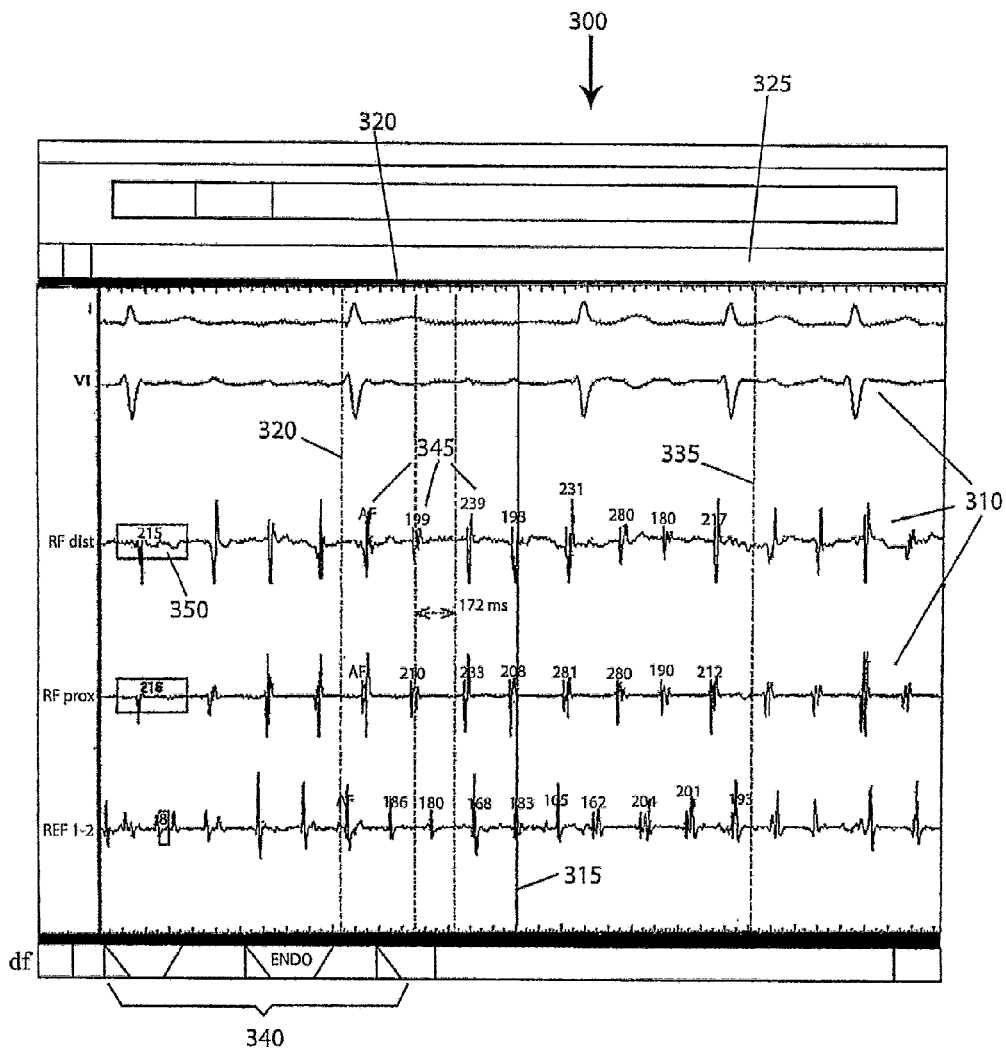
FIG. 3 is an illustration of an electrophysiology system display showing AFCL data in association with defined portions of individual electrocardiograms.

Referring now to FIGS. 2 and 3, a portion of several EGMs 310 are displayed under control of the interface of the EP system. In FIG. 3, the displayed portion of the EGMs are centered relative to a time reference 315, namely, "8:17:48: 257." The EGMs 310 can include composite surface electrograms (denoted I and V1), and individual intracardiac electrograms associated with particular electrode placements (denoted RF dist, RF prox, and Ref 1-2). (The portion displayed can be presented differently when the EGMs are being captured in real-time.) Each of the EGMs is plotted along a time axis and constitutes a time-domain representation of the electrical activity of the heart detected at particular locations that are being monitored on channels, as understood by persons of ordinary skill in the art.

The user interface permits conventional pointer-driven control over multiple objects on the display so as to enable the operator to interact with displayed elements, tabs, pull-down menus and the like. As indicated at step 220, the operator can scroll the displayed portion of previously-recorded EGMs using a conventional pointer such as a mouse, trackball, or touch-pad until an interval of particular interest is displayed on the display 300. The operator can use the pointer to select (e.g., by clicking at a given location on the screen) begin and end points of a segment of interest ("SOI"), and the system will accept such input, as at step 225. If an epoch has been defined, the SOI can be defined by selecting only one point on the screen, such as a beginning point. In FIG. 3, a SOI has been defined and is indicated by interval markers 320,325 at the top of the display, and also by perforated lines 330, 335 that pass vertically through the display of EGMs. Within the SOI, AFCL or other analyses can be made with data made available to EP system software for further processing, such as map creation, diagnosis and ablation therapy. (When working with live data, the epoch is a defined time period, such as the previous five seconds, and the SOI is the epoch leading to the current time during which triggering events are sensed.)

At step 230, the active software process can receive inputs from the operator such as selection of one of the tabs 340 that permit inspection of the captured or processed data in another format (e.g., as a table) or of additional data on the display 300. The selection made at step 230 can also be of a system function such as to analyze selected EGMs (either selected during configuration or thereafter (e.g., by clicking on the label such as "RF dist" or "RF prox" to select or deselect a particular channel)). At step 235, a test is made whether the EP system is to analyze the selected EGMs and determine the AFCL. If not, then any selection made at step 230 can result in other processes being launched, as indicated at step 240.

On the other hand, if the AFCL determination has been invoked (either at step 230 or previously), then the FIR filter operates upon the EGM within the SOI to locate any activation signals within the defined interval that is between lines 330 and 335. More particularly, the FIR filter constitutes a FIR digital signal processor that applies programmed coefficient values against the signals on each selected channel which are fed into the filter as an input. The impulse response of the filter in response to each sampled portion of the EGM signal results in ringing whenever an activation signal event is detected because only those events should match the filter's setting. Preferably, when the filter rings sufficiently strong or "loud" for a given channel, a tick mark 345 is automatically added to the EGM on that channel to indicate each point in time, over the SOI, that corresponds to an activation signal, as indicated at step 250, by including that time location in the data structure for that channel and also by displaying the mark in association with that channel at that time location. Also, threshold values can be used to ignore other signals and prevent false ringing for non activation-signal events.

Other filters and detection schemes can be used to detect activation signals within the EGM; however, the use of a FIR filter is presently a preferred approach.

Next, a further software process is invoked to compute the atrial fibrillation cycle length for the interval between each successive marker, at step 255. There can be no cycle length value for the first activation signal within the SOI because there is no prior activation signal within the interval upon which the cycle length can be computed. Optionally, an indicator such as "AF" can be placed at this first tick mark 345. For each tick mark 345 after the first one in the SOI, an AFCL value is calculated. The AFCL value is as the relative time difference between successive tick marks. In other words, an absolute value of AFCL can be determined for successive activation events using only relative timing differences between the detected activation signals. Thus, for example, for the EGM on channel "RF dist," the atrial fibrillation cycle length for successive activation events is calculated along the SOI, starting at the AF tick mark and continuing until the last tick mark within that interval. Preferably, each computed AFCL value is displayed adjacent its respective tick mark 345 and a set of values are thus determined.

Further, the computed AFCL values are preferably arranged into a data structure that can be used and shared with one or further software processes. With reference briefly to FIG. 3A, data underlying the various graphical objects on the display 300 are stored in a data structure 360 that is accessible by plural software processes. Among the various processes that can access the data are an averaging module, various statistics modules, mapping modules that coordinate the electrophysiological values such as the AFCL values or AAFCL values (discussed below) with other data such as location coordinates, and prediction modules that can augment or modify a map with indicators of potential atrial-fibrillation recurrence points. The data structure associates the data relative to a fixed time-position 315, and stores absolute values relative to that point. This arrangement is advantageous because the absolute AFCL values permit statistical calculations to be made by additional software processes and be stored within a common data structure, if desired. Thus, for example, for a given channel "channel-1," the determined AFCL values, an average value, average variation, the standard deviation, other statistics, and any label for the channel such as "RD dist" or "Ref 1-2" can be stored in the data structure as each data is established. In addition, the FIR filter coefficient values or neural network settings can be stored to permit recreation of the data or alterations to the data by indexing to that particular time-position point. The contents of the data structure 360 can supply information to construct and destruct data points as described in U.S. patent application Ser. No. 09/943,408, filed Aug. 30, 2001, entitled Software Controlled Electrophysiology Data Management, which is hereby incorporated by reference as if set forth in its entirety herein.

In FIG. 3, the computed AFCL values present significant variation over the interval, ranging from 199 ms to 239 ms. However, it should be recalled that the EGM is being sensed by one electrode (or electrode pair) representing signals at one portion of cardiac tissue. Accordingly, it is preferred that a further software process be invoked to compute and display an average AFCL ("AAFCL") of each channel over the SOL and more preferably display the AAFCL in association with each respective channel. For example, the AAFCL 350 for channel "RF dist" has the value "215" and is set-off from the remainder of the display by highlighting (illustrated as a box, but other or additional highlighting such as the color, size, or formatting of the font can be used). Alternatively, the AAFCL can be displayed in individual or composite bar graph indicators which are especially useful when real-time analysis is being performed. An individual bar graph can provide a graphical display to the operator of the average on a given channel being monitored, whereas a composite bar graph can graphically inform the operator of the overall average AFCL among the channels. Color coding can show which channels are above or below the overall average, and high- and low-water-marks can be provided to show the maximum deflection of the bar graph during the observed interval or procedure. The average can be updated as a moving average over a pre-selected number of beats.

At step 260, the AAFCL is calculated by the software by summing the AFCLs at each tick mark in the interval SOI and dividing the sum by the number tick marks minus 1. Expressed mathematically, $$AAFCL = (\Sigma|_{SOI} AFCL)/(N-1),$$

where N is the total number of tick marks within the interval SOI. An average AFCL determination is desirable when operating on live data because the variation and scrolling of discrete AFCL data points could be difficult to assess by an operator, yet the average value can provide a more stable reference for the operator to consider and for map creation. A bar graph representation of parameters such as the AAFCL is desirable as well in order to improve comprehension by an operator of the computed information.

Other parameters can be calculated at step 265 by the same or further software processes to develop further information on the heart being analyzed for presentation on the display 300 in association with a respective EGM, as indicated at step 270. Such further parameters can include statistics that can be used to gauge the data being collected and may comprise variance calculations among the AFCL values or the standard deviation within the data set. These statistics can assist in developing a map of AFCL, with interpolated and extrapolated contours being derivable between the individual values and across EGM channels, assuming that the general location of the sensing electrodes is known such that the collected data can be rendered in a meaningful way.

The other parameters can include a Fourier analysis performed using a fast Fourier transform, for example, to identify dominant or recurrent frequencies in the data and their locations. Such information can be used to predict and identify on the display 300 a location for ablation. For example, variance of the cycle length in the time domain may influence the frequency domain representation of the data, and so the frequency domain representation of AFCL values for a given electrocardiogram can provide utility in identifying an epicenter of a focus. As a simple case, a frequency domain representation can comprise frequency plotted along one axis, position along another axis (or two axes), and amplitude along a third axis or in a color if three axes have been used. The fast Fourier transformation (FFT) technique is described in Theory and Application of Digital Signal Processing, L. R. Rabiner and B. Gold, Prentice-Hall, Englewood Cliffs, N.J. 1975 p. 357-381. As a result of the transformation into the frequency domain, a number of parameters can be calculated and displayed such as the frequency of maximum amplitude and its location relative to the sensing electrodes, or a frequency analysis over the SOI.

Any of the values or statistics concerning AFCL can be displayed or not in response to user control received as an input through the interface manager 160. These values and statistics can be displayed in bar graphs that provide a graphical representation of that calculation for any given channel or as a composite derived from the data on various channels.

At step 275, the operator can input adjustments that he or she may wish to make to the markers based on his or her professional interpretation of the EGMs. More particularly, the operator can delete a given tick mark (e.g., because one of the markings appears to be a double potential resulting from a conduction block), or insert a tick mark even if its potential did not satisfy the filter's trigger, which is tested at step 280. If such adjustments are made, they have the effect of changing the absolute AFCL value of the next tick mark in the SOI after that point of adjustment, assuming that the adjusted AFCL value was not the last tick mark in the interval. When a tick mark is inserted, an AFCL value is computed for that new tick mark, and the AFCL value for the next tick mark is re-computed, as described above. The software recalculates these particular values by looping back to step 255, and preferably updates the data structure 360 accordingly.

Alternatively, the operator may wish to shift a tick mark 345 to a new location if the operator disagrees with the position that the EP system 100 placed that tick mark. As noted above, the system places marks in accordance with the impulse response of the FIR, which in turn is a function of the coefficient values used by the FIR filter. As a default, for example, the FIR may ring loudest at the onset of the fastest deflection in the EGM (as shown). The operator, however, may prefer a different triggering characteristic for a given patient, and can drag a given tick mark to a new location. This has the effect of adjusting the coefficient values of the FIR filter itself, which is tested at step 285 and if true, causes all of the data for each of the selected channels to be updated based on the filter response using the newly-set characteristic. The software effects the re-calculation of all of this data by looping back to step 250, preferably also updating the data structure 360.

Other inputs are possible, such as selecting to display a map of the AFCL data or an image of the distal portion of one or more catheters within the heart at the locations where the data is being sensed. Other functions and operations of the EP system 100 are accessed by an input that causes the process of FIG. 2 to end at step 290.

When using a electrode array, such as an expandable wire mesh in which a multiplicity of electric sensors are positionable within a chamber, multi-channel data can be gathered with AFCL points for the multiplicity of sensors thereby providing data useful in defining a high-resolution AFCL map.

Figure 4:
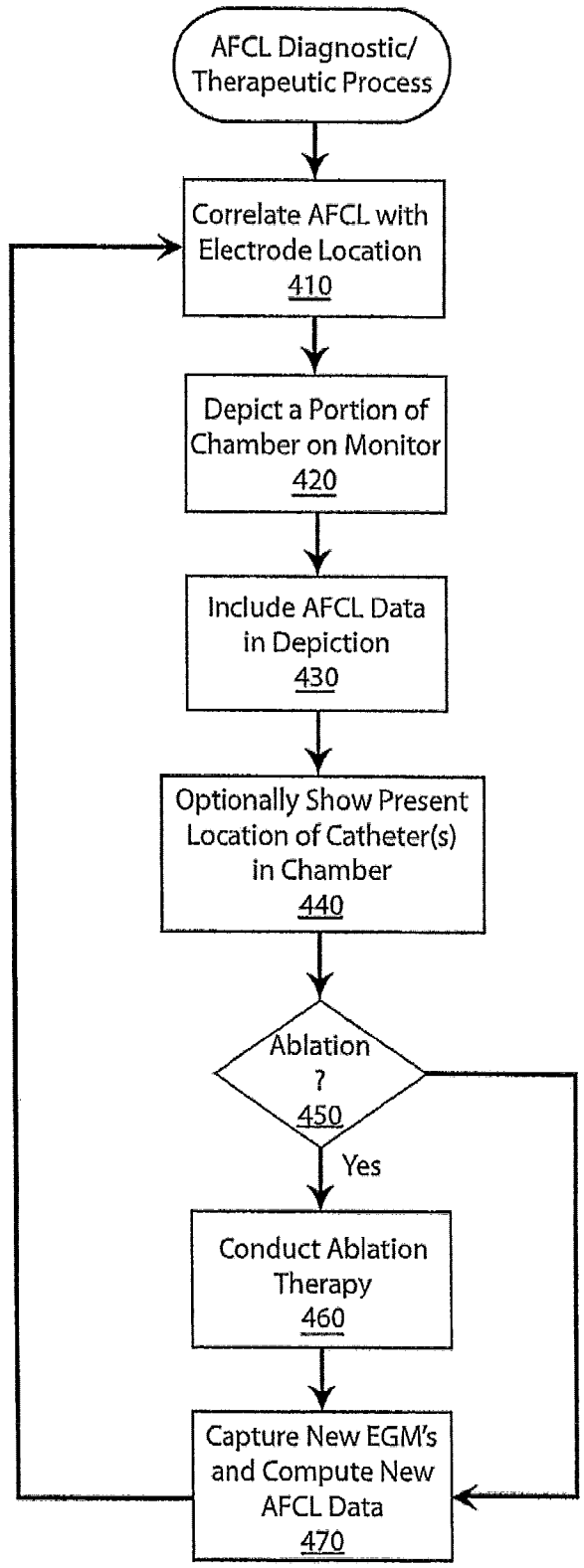
FIG. 4 is a flow diagram of a diagnostic and optionally therapy/intervention process that utilizes AFCL data.

Referring now to FIG. 4, a diagnostic process for mapping data relating to atrial fibrillation cycle length is described in connection with a live procedure in which ablation therapy is possible.

When an electrophysiology system 100 configured with software as described above is provided, AFCL values and information derived therefrom are available for mapping on a monitor connected to the EP system. As noted above, AFCL data is calculated from EGMs associated with particular electrodes on a catheter, and more preferably on a multi-electrode catheter. As noted below, AFCL data can be a frequency domain transformation of the EGM signals. Each electrode has a location which is tracked in a conventional manner, and the AFCL data is correlated at step 410 with the location of a particular electrode at which it was positioned when the EGM data was provided to the EP system. The AFCL data to be mapped can be, for example, an individual value that is captured during the SOI, but more typically comprises an average AFCL of all AFCLs computed over the SOI. Alternatively, the AFCL data can be a statistic concerning the AFCL data such as the AFCL variance or AFCL standard deviation. Within the meaning of "AFCL data," the inventors include data resulting from a Fourier transformation of the AFCL values such as the peak frequency, peak frequency variation, and standard deviation in the frequency. Preferably, the operator controls the nature of AFCL data to be displayed by interacting with the interface manager 160 and inputs his or her selection using a pointer.

At step 420, a portion up to the entirety of a heart chamber is depicted on a monitor. It Can be the same monitor 300 that displays the EGM data, or a different monitor. Preferably, the depiction is shown in its own window or frame. The depiction can be a simple wire frame rendering or cartoon (model) of the chamber, and can be depicted in two or three dimensions. For example, a wall of the atrium might be depicted in step 420 within a window 500, as shown in FIG. 5.

Figure 5:
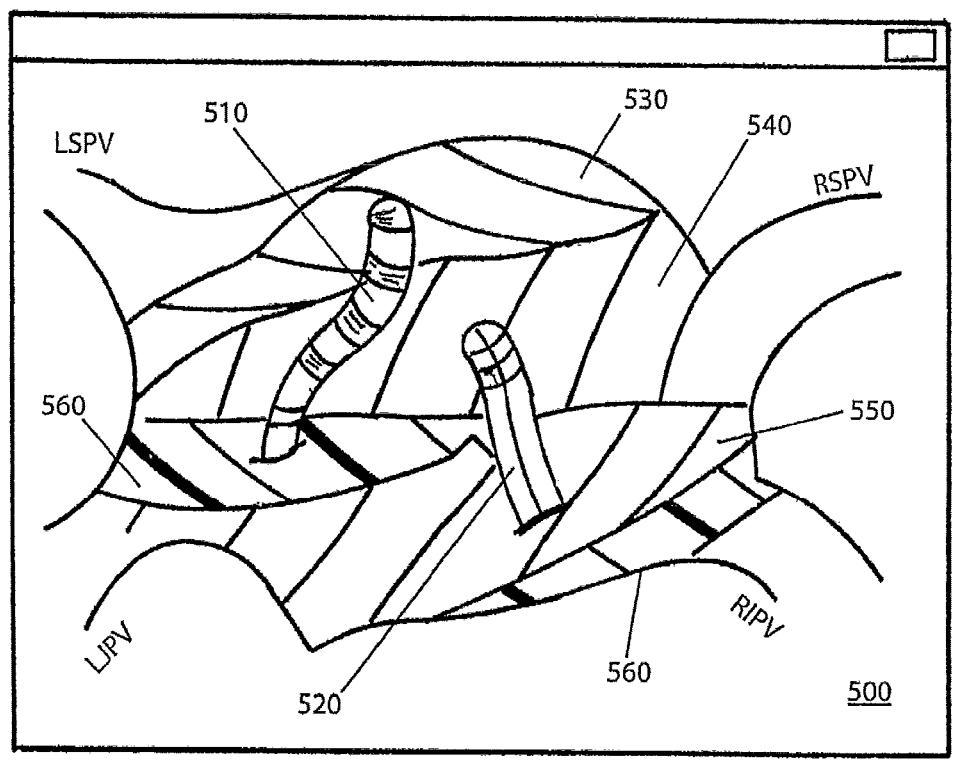
FIG. 5 is a schematic illustration of a display showing an AFCL data map.

At step 430, the software includes the AFCL data in the depiction, as illustrated in FIG. 5. Preferably, the AFCL data is presented in color, though in FIG. 5 four isochronal bands of AAFCL values 530-560 are illustrated and differentiated from one another using differing hatch lines. The map can be a color isochronal map showing the different AF cardiac cycle lengths across the heart wall which can be identified by operating EP physician to assess the nature of the substrate that may be vulnerable to arrhythmic trigger. In the event that there are isochronal markings on the map, the differences in cycle length across the atrial substrate can provide a visual indication to EP physicians (a) if the atrial substrate is (still) susceptible to AF, or (b) which region or regions of atrial tissue are more vulnerable to recurrence of AF.

The isochronal map provides a visual tool to EP physicians to identify the vulnerable arrhythmic substrate and find the targeted area for intervention. The isochronal map provides an evaluation tool to assess the results of the treatment such as the effectiveness of PV isolation and the need for a left isthmus line, etc. The isochronal map provides a predictive value of the arrhythmias treatment, e.g. the outcome of the catheter ablation for the treatment of atrial fibrillation, as well as the likelihood of recurrence. The treatment decision could be made based on the detected AFCL at a specific location, e.g. to create focal or linear lesion in the local heart tissue with the shortest AFCL to create a conduction block or modify the substrate accordingly.

The map need not present AFCL data in isochronal form. As noted above, frequency domain transformations of AFCL data can provide data and derived statistics for additional maps based on AFCL data to inform the physician of the nature of the cardiac substrate.

Optionally, an image or identifier of the current location of the catheter(s) within the mapped chamber can be shown in the map as well, as indicated at step 440. In FIG. 5, catheters 510 and 520 are illustrated.

A decision can then be made to determine if treatment need be applied, e.g., to apply energy to block the re-entry circuits so as to modify the substrate, as tested at step 450. For example, in conventional atrial fibrillation ablation therapy, an ablation procedure might seek to isolate one or more pulmonary veins, whereas the software of the present invention can be utilized to determine if extra lesions are indicated to treat the atrial substrate outside of the pulmonary veins. Alternatively, AFCL diagnostics can be used to make an initial determination of where in a heart a lesion is to be made based on AFCL data.

In connection with further aspects of the invention, diagnostic determinations can be performed as a spectral analysis using frequency-domain representations of the electrogram signals, and in particular with regard to either the regularity in the dominant frequency observed at multiple cardiac locations (including among multiple chambers) or a gradient observed in the dominant frequencies observed among such locations. Empirically, the mean dominant frequency (DF) from 30 second EGM recordings have been found to correlate well with manually measured mean AFCL (measuring a bipolar signal in the coronary sinus using a FFT window length of 4096 msec (resolution 0.244 Hz) and a sliding window of every 1 sec) which provides a basis for a new paradigm in diagnostic analysis of atrial fibrillation in which spectral rather than temporal analysis is correlated with cardiac locations in order to identify foci. It has been also been empirically demonstrated that the mean DF correlates well with mean uRI (defined below) and mean AFCL correlates well with the standard deviation (SD) in the cycle length.

Software configured in accordance with this aspect of the invention executes in the processor 140 and transforms time-domain representations of conventional EGMs into a frequency domain representation, for example, using a FFT over a time interval. Preferably, the time interval is at least about 4 seconds in order to ensure sufficient resolution, and preferably is a time interval on the order of about 4 seconds to about 10 seconds so that the clinician can strike a balance between sufficient resolution and speed of data analysis. The frequency-domain representation can be obtained for each electrode of the catheter in a unipolar manner or for each bipole-electrode pair, and each such frequency domain representation can be illustrated as a plot of frequency verses magnitude, or can be represented by other parameters or statistics such as the dominant frequency (DF) within the plotted sample. A variety of conventional algorithms can be employed in order to perform the FFT, including by way of example a classic FFT algorithm or a PD Welch algorithm.

Figure 6:
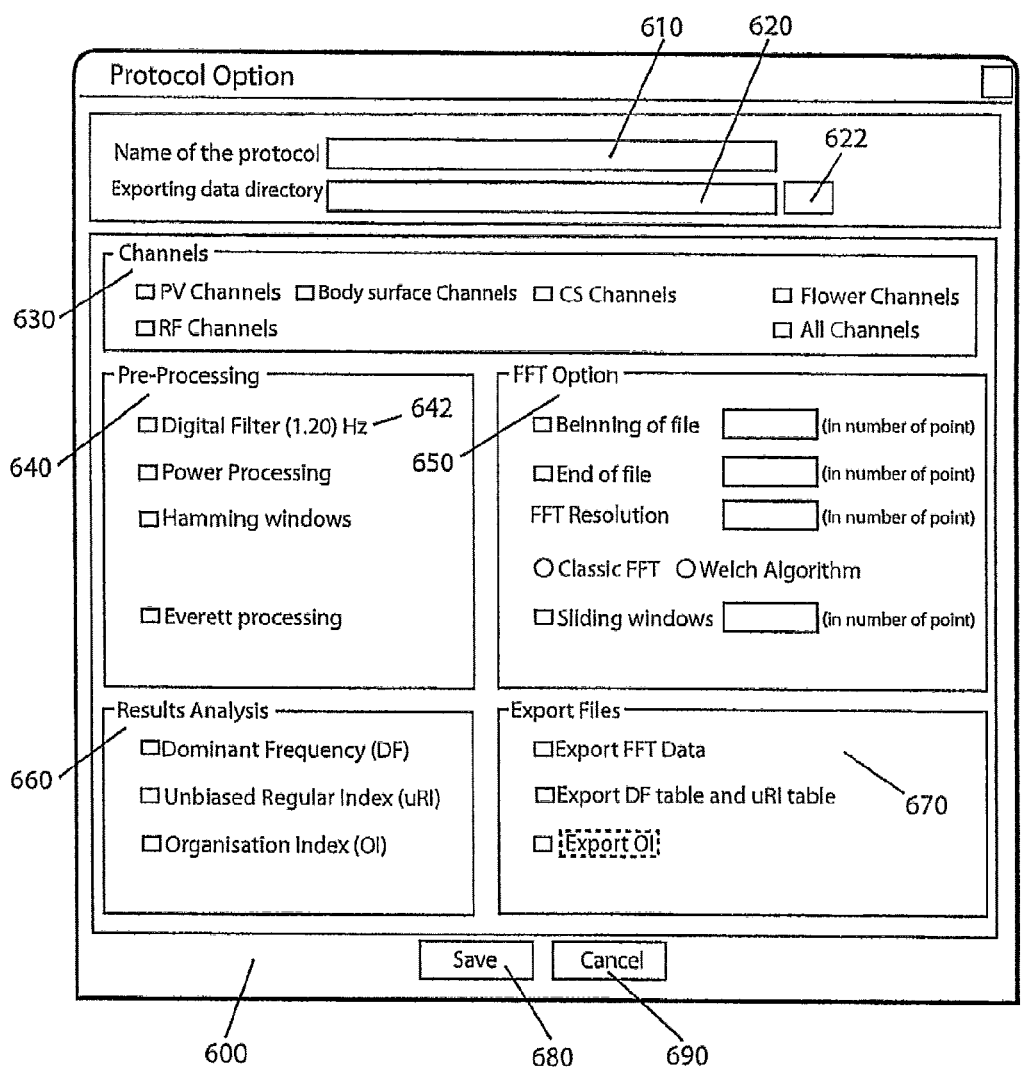
FIG. 6 illustrates an exemplary screen of the interface which is suitable for selecting or establishing the protocol for generating a frequency domain representation of electrogram signals.

Referring now to FIG. 6, the protocol to be used in establishing the frequency-domain representation ("FDR") of one or more EGM signals can be entered through a protocol selection screen 600 which is preferably part of the interface manager 160. All of the parameters necessary to compute FFT are stored in a protocol, and previously-stored protocols can be loaded or removed using suitable controls provided on at least the main screen 800 (See area 820 of FIG. 8) The protocol selection screen 600 provides controls with which a user can interact in order to establish the conditions upon which the FDR is generated. The protocol to be used can be retrieved by entering a protocol name into text box 610. Entry of data in this box and pressing an enter key preferably causes the interface manager to search for and retrieve previously-saved protocol settings which can be presented to the user as selections in the remaining selections on the protocol selection screen. The user can identify a directory for exporting data by entering suitable path information into text box 620. The user can browse for existing paths using button 622. A selection of channels is provided in region 630, from which the user can select particular channels for FDR display or all channels. The user has the option of selecting pre-processing of the EGM signals in region 640, as described below. The time interval for applying the FFT to the EGMs as well as the resolution for the mathematical processing is set in region 650, and can commence with regard to existing data files (e.g., from the beginning to last point in the file or from arbitrary points therein) or by repeatedly sliding the time interval in a user-settable interval. The resolution is the number of points on which the FFT is computed (the frequency resolution (Hz) is 1/FFT resolution). The algorithm that can be chosen in the present implementation is either "classic" or "Welch," although other algorithms can be employed without loss of generality. The Welch algorithm compute an average FFT over a window that is 2 times larger than the FFT resolution. Details about FFT and Welch processing can be found in the following references: M. Hayes, *Statistical Digital Processing and Modeling*: John Wiley & Sons, 1996; P. Stoica and R. L. Moses, *Introduction to Spectral Analysis*. Englewood Cliffs, N.J., 1997; and P. D. Welch, "The Use of Fast Fourier Transform for Estimation of Power Spectra: A Method Based on Time Averaging Over Short Modified Periodograms", *IEEE Transaction on Audio and Electroacoustics*, vol. AU-15, pp. 70-73, 1967. If sliding windows are desired, the user checks the box "sliding windows" and specifies the distance in sample between two consecutive windows; in that case, a FFT is computed every specified number of samples.

The display of results can include any of several parameters selectable, as at region 660, and can include by way of example a Dominant Frequency (DF), an unbiased Regularity Index (uRI), and an Organization Index (OI). The content of data exported to a file can be user set as well, as indicated at region 670, and can be flagged to receive the FFT, tables including parameters relating to the FDR such as the DF and the uRI for each FFT, and the OI for each FFT. A new protocol with these settings can be saved or canceled using buttons 680, 690, respectively. The data can be exported in a number of manners, however, it is presently preferred that there be one export file for each computed channel with FFT values of the spectrum, each such file being compatible with spreadsheet software such as Excel made available by the Microsoft Corporation.

Preferably, the "DF" is the frequency for which the spectrum is maximal in the 1 Hz to 20 Hz band. "uRI" is an index that measure the relative power of DF and harmonics peaks over all spectrum in the 1 Hz to 20 Hz band. "OI" is an index that measures the narrowness of the DF and harmonics peaks. One FFT can be computed every second in order to monitor DF, uRI and CA over time, and a sliding window can be used to encompass more than one second's worth of data.

The pre-processing selections in region 640 provide the user with several options that affect the data that is submitted to the FFT algorithm. The digital-filter option 642 can be 4th order bandpass Butterworth filter between 1 and 20 Hz. The filter permits band-pass filtering of the EGM data prior to FFT computation to eliminate frequencies outside of the passband or above the cut-off of a low pass filter. The pre-processing can take on other forms such as a linear function (e.g., to digitally amplify or attenuate the signal) or a non-linear function (e.g., absolute value or squaring (that is, raising to the second power)). Selection of the power processing option causes computation of the power of the EGM signal, that is, the square of the signal, and so the FFT will be of the power-signal rather than the raw EGM data, and the resulting plot is called the Power Spectral Density, within which the same parameters discussed above can be observed and analyzed. The "Hammings windows" option allows the user to use a smoothing window before FFT computation; this option is only valid if "classic FFT" is computed, when the Welch algorithm is selected, Hamming window is automatically applied. The "Evrett" check box is a special pre-processing and methodology to compute FFT, and details of this protocol are described in T. Everett, J. Moorman, L. Kok, J. Akar, and D. Haines, "Assessment of Global Atrial Fibrillation Organization to Optimize Timing of Atrial Defibrillation", *Circulation*, vol. 103, pp. 2857-2861, 2001.

Figure 7A:
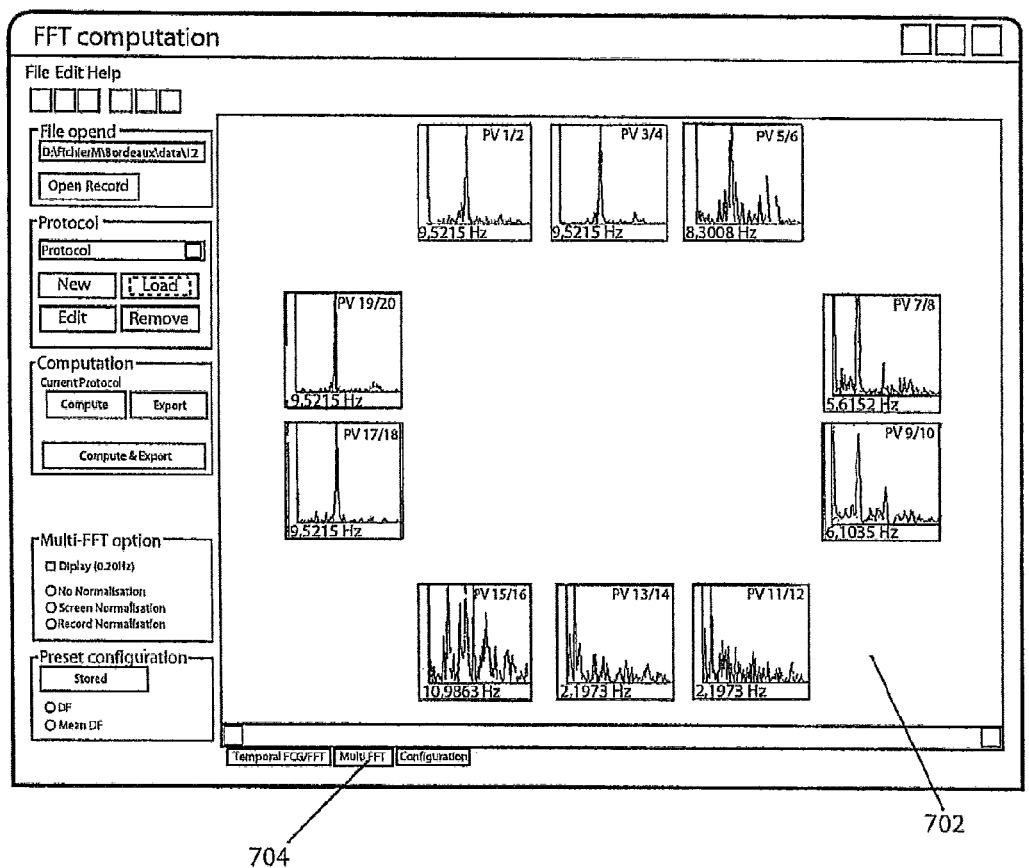
FIGS. 7A, 7B and 7C illustrate exemplary screens showing frequency domain information in association with the relative locations of plural electrodes, and, in the case of FIG. 7B, in association with the absolute locations of plural electrodes.
Figure 7B:
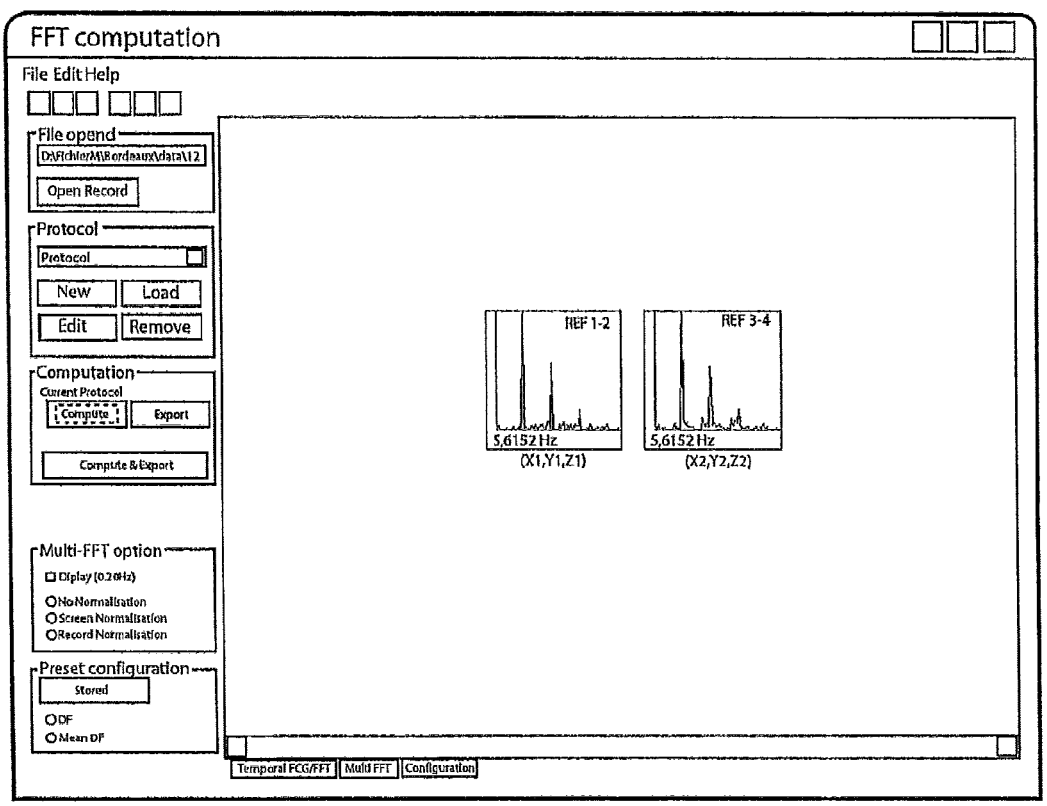
Figure 7C:
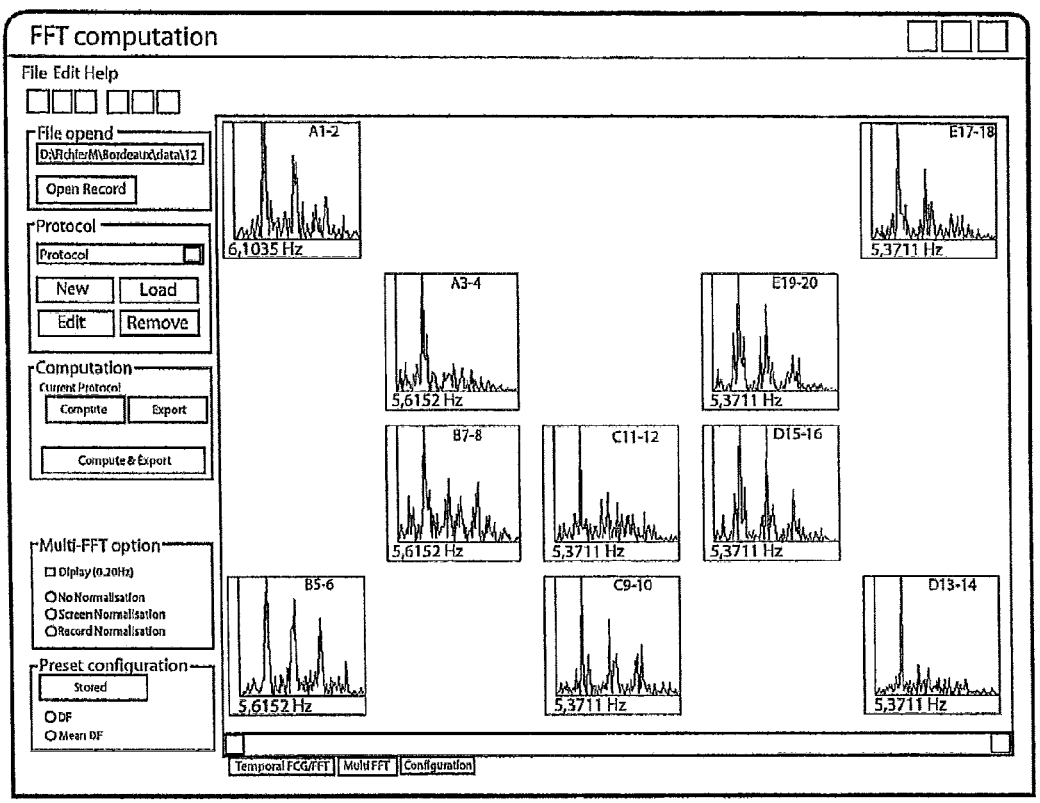

FIGS. 7A, 7B and 7C illustrate an exemplary display of the spectral content of captured or real-time EGM signals from which the regularity in the dominant frequency observed at multiple cardiac locations can be seen, as well as any gradient in the dominant frequencies among such locations. Optionally, the orientation of the gradient can be highlighted to the user in the window or frame 702, and maps of same value DF or other parameters and statistics can be provided in the window or frame 702. In FIG. 7A, the relative orientation of ten electrode pairs for a lasso catheter are illustrated in a window or frame 702 that can be displayed on the monitor 300, such as by selecting tab 704. As can be appreciated, the electrodes of this catheter construction assume a loop-like shape within the cardiac chamber in which they are deployed.

In FIG. 7B, two electrode pairs are displayed for a four pole ablation catheter and in FIG. 7C ten electrode pairs for a multi-splined catheter are illustrated. In each case, the relative orientation of the electrodes to one another is displayed in the window or frame. Optionally, the display configuration can include the DF (which is selected in these Figures) or a mean DF value. The AFCL can also be displayed in a similar manner.

In addition, a numeric value of a dominant frequency (DF) within the frequency domain representation is identified, as well as which electrodes on the body of the catheter are associated with each particular frequency domain plot, as shown in the window or frame 702. Alternatively or in addition, the uRI and OI parameters and other parameters and statistical information (including the gradient in any change in dominant frequency from electrode-to-electrode) can be displayed in association with any of the electrodes. Thus, for example, the uRI and OI parameters can be shown together with the FDR for a given electrode, instead of the FDR yet at the relative or mapped location of that electrode, or separately in a table or plot.

Advantageously, the FDR includes a DF calculation for each electrode (electrode pair) position, and multiple DF calculations are displayed on the monitor 300 for data that has been acquired simultaneously across locations in one or more heart chambers. This can be done using one or more catheters, each having multiple poles. A large area, high density, mapping catheter is suitable for this purpose. Optionally, a map of iso-DF calculations can be presented using data acquired either at the same time or at different times as an alternative presentation format to provide the clinician with another representation of the response of the cardiac substrate. Simultaneous acquisition of data is preferred due to the chaotic nature of the cardiac signals during fibrillation.

In a preferred implementation, a localization routine is utilized to provide location information concerning the position of each electrode (electrode pair) within the cardiac chamber and thereby provide information to the user that can be used in subsequent analysis or for repositioning the catheter and its electrodes. As shown in FIG. 7B, an absolute location of the electrode pair Ref 1-2 can be identified in the region 702 as a location (X1, Y1, Z1) and the electrode pair Ref 3-4 can be identified in the region 702 as a location (X2, Y2, Z2). Cartesian, spherical or other coordinate systems can be employed, but Cartesian is preferred. "Absolute location" as used herein refers to an identifiable location of any particular electrode that can be re-established even if a catheter or its electrodes have been moved around the heart.

From FIG. 7 it can also be appreciated that the user interface provides on the monitor FDR plots for each recording channel that has been selected (i.e., through interaction with the area 630 of the protocol selection screen 600). Thus, an FDR plot is available for each anatomic location that is in contact with an electrode or electrode bipole pair. The information being displayed is captured as an event during a given time epoch that has been defined by the user using the interface. Multiple events can be captured to determine repeatability of the FDR over time. The captured data can be reviewed at a later time, for example, to compare the electrical response of pre- and post-operative cardiac substrate.

Figure 8:
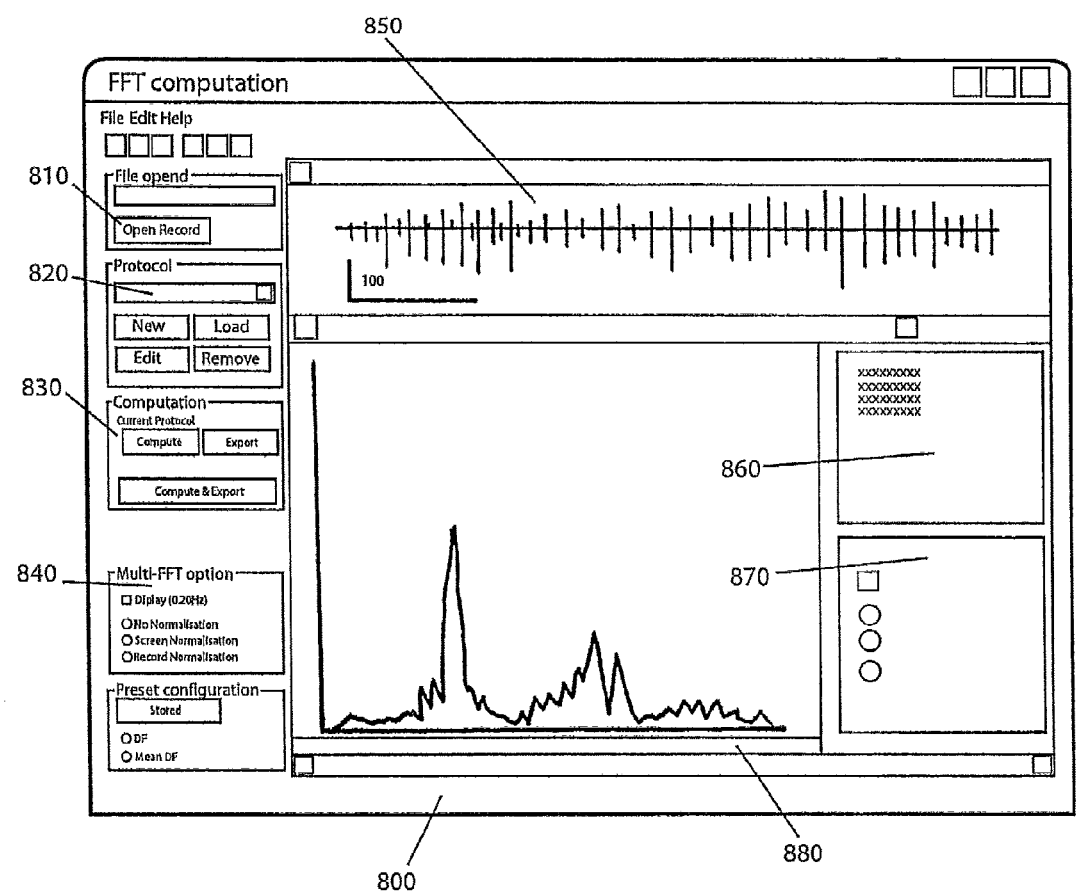
FIG. 8 illustrates an exemplary screen of the interface which is suitable for displaying simultaneously both time- and frequency-domain representations of electrogram signals, as well as further information as shown in the figure and described below.

Referring now to FIG. 8, a main screen 800 of the interface manager for accessing the FDR of an EGM is shown. From the main screen the user can select a recorded file to analyze (area 810), load or edit a protocol and select the active protocol (area 820), start the FFT computation (area 830) and export results achieved using the selected protocol, observe information on the current channel being drawn (area 840) including the channel name, the leads, and a portion of the EGM, for instance, 5000 samples or so at a sample rate of 1000 Hz (in which case the screen displays 5 seconds of the EGM signal at any given time, with a scroll bar permitting navigation through the EGM, as desired), observe a temporal plot of the EGM on the selected channel (area 850), observe information on the FFT parameters used to draw in area 880 (area 860), specify options for the plot of the FFT in area 880 (area 870) including normalization, and observe the spectral content of the current channel over the time interval (area 880).

As can be appreciated from FIG. 8, the user can be provided with a display of both AFCL and FFT information, for one or more channels. While AFCL information can be adequate to characterize a focus of the AF by identifying the shortest cycle length, not all electrograms permit measurement of AFCL (e.g., the data may be fragmented). In any event, the FFT can reveal a dominant frequency and thereby provide information concerning the location of a focus, and this may be a clearer indicator of the location of the focus than the time-domain-based AFCL in cases in which there is fragmentation of the electrogram as that make an AFCL value difficult to discern. In part, embodiments of the present invention can provide a clinician with access to both analyses, displayable either individually or simultaneously.

Area 870 controls the normalization of the FFT. If "no normalization" is checked, the maximum signal of the displayed FFT is the upper point of the area. However, if "channels normalization" is used, the FFTs are normalized by the maximum value of the spectrum for the displayed channel. If "record normalization" is checked, the FFT is normalized by the maximum value of the spectrum over the entire record. The user can also choose to only display the pass-band of 1 Hz to 20 Hz using the check box in area 870.

If the operator elects to ablate tissue, then the process flow proceeds to step 460 at which ablation energy is permitted to flow to the indwelling catheter(s), in accordance with conventional procedures. Thereafter, at step 470, new EGMs are sensed by the electrodes on the catheters 510, 520 and new AFCL data is computed, as described above in connection with FIG. 2. On the other hand, if ablation is not requested, then the flow advances to step 470, described above. Since the diagnostic and optional therapy/intervention procedure are performed live, the epoch for the SOI is defined during configuration, as described above, and includes a time period leading up to current time (such as 5 seconds).

Optionally, pre- and post-ablation maps can be superimposed upon one another to provide a temporal superimposition of information that can indicate whether the ablation has been adequate to block a reentry circuit and/or to suitably modify the substrate.

While the foregoing description has been directed primarily to atrial fibrillation, the foregoing methods and systems can be applied in the diagnosis and treatment of ventricular fibrillation, and in the diagnosis and treatment of atrial fibrillation in which one or more electrodes and/or catheters are disposed in one or both of the ventricles as well as in one or both of the atria.

Having thus described preferred embodiments of the present invention, it is to be understood that the foregoing description is merely illustrative of the principles of the present invention and that other arrangements, methods, and systems may be devised by those skilled in the art without departing from the spirit and scope of the invention as claimed below.

What is claimed is:

1. A method for annotating an electrocardiogram with an atrial fibrillation cycle length (AFCL) value that is displayable on a display of an electrophysiology system, comprising the steps of:
   (a) providing an electrocardiogram signal within the electrophysiology system;
   (b) accepting input to the electrophysiology system to define a time segment of interest within the electrocardiogram signal;
   (c) locating successive activation signals within the time segment of interest on each electrocardiogram signal;
   (d) determining one or more average AFCL values using the located successive activation signals and an AFCL statistic from the one or more average AFCL values;
   (e) associating on the display of the electrophysiology system at least one of the determined average AFCL values and the AFCL statistic together with the electrocardiogram signal;
   (f) depicting a rendering of a portion of at least one heart chamber; and
   (g) including the AFCL statistic in the rendering.

2. The method of claim 1, wherein the locating step comprises applying the electrocardiogram signal within the time segment of interest to an input of an FIR filter and outputting a stream of signals from the FIR filter which includes the located successive activation signals.

3. The method of claim 1, including the additional step of automatically marking the located successive activation signals on the display in association with the electrocardiogram signal.

4. The method of claim 3, wherein the average AFCL values include at least a first set of values which correspond to the absolute value of the time interval between each successive activation signal that has been located.

5. The method of claim 4, wherein the first set of AFCL values is displayed on the display of the electrophysiology system proximate to the located successive activation signals.

6. The method of claim 1, wherein the rendering is a model of the at least one heart chamber.

7. The method of claim 1, wherein the rendering is a captured image of the at least one heart chamber.

8. The method of claim 7, wherein the captured image is captured by a technique selected from the group consisting of: fluoroscopy, magnetic resonance imaging, computer tomography, ultrasound imaging, and ultrasound echoing.

9. The method of claim 1, wherein the rendering is depicted in a window separate from the electrocardiogram signal.

10. The method of claim 9, wherein the window is presented on a second display independent of the display of the electrophysiology system.

11. The method of claim 1, wherein the electrocardiogram signal is provided from a first electrode of a multi-electrode catheter and wherein there are plural electrocardiogram signals associated with respective plural additional electrodes on the multi-electrode catheter, each of said plural electrocardiogram signals having at least one AFCL statistic associated therewith over a time segment of interest that overlaps with the time segment of interest for the electrocardiogram signal from the first electrode.

12. The method of claim 11, wherein the step of including the AFCL statistic in the rendering comprises coordinating a position of one or more of the electrodes of the multi-electrode catheter with a respective AFCL statistic.

13. The method of claim 12, including the additional steps, after an ablation procedure has been initiated, of determining one or more additional AFCL values and statistics within the at least one heart chamber and depicting said additional AFCL statistics in a second rendering of the at least one heart chamber.

14. The method of claim 1, wherein the step of providing the electrocardiogram signal includes obtaining signals from an intracardiac lead and displaying the signals on the display.

15. The method of claim 1, wherein the time segment is defined based on an input provided by a user.

16. A method for annotating an electrocardiogram with an atrial fibrillation cycle length (AFCL) value that is displayable on a display of an electrophysiology system, comprising the steps of:
   (a) providing an electrocardiogram signal within the electrophysiology system;
   (b) accepting input to the electrophysiology system to define a time segment of interest within the electrocardiogram signal;
   (c) locating successive activation signals within the time segment of interest on each electrocardiogram signal;
   (d) determining one or more average AFCL values using the located successive activation signals and determining an AFCL statistic from the one or more average AFCL values;
   (e) associating on the display of the electrophysiology system at least one of the determined average AFCL values together with the electrocardiogram signal; and
   (f) depicting a rendering of a portion of at least one heart chamber, and including the AFCL statistic in the rendering.

17. The method of claim 16, wherein the locating step comprises applying the electrocardiogram signal within the time segment of interest to an input of an FIR filter and outputting a stream of signals from the FIR filter which includes the located successive activation signals.

18. The method of claim 16, including the additional step of automatically marking the located successive activation signals on the display in association with the electrocardiogram signal.

19. The method of claim 18, wherein the average AFCL values include at least a first set of values which correspond to the absolute value of the time interval between each successive activation signal that has been located.

20. The method of claim 19, wherein the first set of AFCL values is displayed on the display of the electrophysiology system proximate to the located successive activation signals.

21. The method of claim 16, wherein the rendering is a model of the at least one heart chamber.

22. The method of claim 21, wherein the rendering is a captured image of the at least one heart chamber.

23. The method of claim 22, wherein the captured image is captured by a technique selected from the group consisting of: fluoroscopy, magnetic resonance imaging, computer tomography, ultrasound imaging, and ultrasound echoing.

24. The method of claim 16, wherein the rendering is depicted in a window separate from the electrocardiogram signal.

25. The method of claim 24, wherein the window is presented on a second display independent of the display of the electrophysiology system.

26. The method of claim 16, wherein the electrocardiogram signal is provided from a first electrode of a multi-electrode catheter and wherein there are plural electrocardiogram signals associated with respective plural additional electrodes on the multi-electrode catheter, each of said plural electrocardiogram signals having at least one AFCL statistic associated therewith over a time segment of interest that overlaps with the time segment of interest for the electrocardiogram signal from the first electrode.

27. The method of claim 26, wherein the step of including the AFCL statistic in the rendering comprises coordinating a position of one or more of the electrodes of the multi-electrode catheter with a respective AFCL statistic.

28. The method of claim 27, including the additional steps, after an ablation procedure has been initiated, of determining one or more additional AFCL values and statistics within the at least one heart chamber and depicting said additional AFCL statistics in a second rendering of the at least one heart chamber.

29. The method of claim 16, wherein the step of providing the electrocardiogram signal includes obtaining signals from an intracardiac lead and displaying the signals on the display.

30. The method of claim 16, wherein the time segment is defined based on an input provided by a user.

* * * * *